(12) United States Patent
Werth

(10) Patent No.: US 8,328,457 B2
(45) Date of Patent: *Dec. 11, 2012

(54) SANITARY CLAMP

(75) Inventor: Albert A. Werth, Kewadin, MI (US)

(73) Assignee: Twin Bay Medical, Inc., Williamsburg, MI (US)

( * ) Notice: Subject to any disclaimer, the term of this patent is extended or adjusted under 35 U.S.C. 154(b) by 682 days.

This patent is subject to a terminal disclaimer.

(21) Appl. No.: 12/175,712

(22) Filed: Jul. 18, 2008

(65) Prior Publication Data

US 2009/0119886 A1    May 14, 2009

Related U.S. Application Data

(60) Provisional application No. 60/950,968, filed on Jul. 20, 2007.

(51) Int. Cl.
*B25G 3/24* (2006.01)
*F16B 2/02* (2006.01)
*F16B 7/04* (2006.01)

(52) U.S. Cl. ........ 403/289; 403/290; 403/313; 285/415; 24/16 R

(58) Field of Classification Search .............. 403/289, 403/290, 312–314; 285/411, 414, 415; 24/16 R, 24/20 R, 284, 285; 248/74.1, 74.3, 74.4, 248/62, 230.4; 411/182

See application file for complete search history.

(56) References Cited

U.S. PATENT DOCUMENTS

| 850,731 | A |   | 4/1907 | Christensen et al. |
|---|---|---|---|---|
| 1,441,154 | A | * | 1/1923 | Johnson ........................ 24/20 R |
| 3,860,997 | A | * | 1/1975 | Van Riper et al. .......... 24/16 PB |
| 3,915,167 | A |   | 10/1975 | Waterman |
| 4,049,301 | A |   | 9/1977 | Schenk |
| 4,212,303 | A |   | 7/1980 | Nolan |
| 4,247,076 | A |   | 1/1981 | Larkin |
| 4,442,994 | A |   | 4/1984 | Logsdon |
| 4,487,205 | A |   | 12/1984 | Di Giovanni et al. |
| 4,557,024 | A | * | 12/1985 | Roberts et al. .............. 24/20 TT |
| 4,588,160 | A |   | 5/1986 | Flynn et al. |
| 4,736,925 | A |   | 4/1988 | Kamstrup-Larsen et al. |
| 4,942,886 | A |   | 7/1990 | Timmons |
| 4,944,485 | A |   | 7/1990 | Daoud et al. |
| 5,203,056 | A |   | 4/1993 | Funk et al. |
| 5,238,218 | A |   | 8/1993 | Mackal |
| 5,271,649 | A |   | 12/1993 | Gromotka |

(Continued)

OTHER PUBLICATIONS

Notification of Transmittal, International Search Report and Written Opinion dated Dec. 29, 2010 from the corresponding International Application No. PCT/US2010/032670 filed Apr. 28, 2010.

(Continued)

*Primary Examiner* — Michael P Ferguson
*Assistant Examiner* — Eric Chau
(74) *Attorney, Agent, or Firm* — Young Basile

(57) ABSTRACT

A sanitary clamp made of high molecular weight thermoplastic polymer for connection to a barb connector having one end with a funnel formation. The sanitary clamp includes a pair of essentially semi-circular members having a pivotal connection at one of the ends of each member and a locking connection at the other ends of each member. The semi-circular portions of the members are configured to sealing and secure a pair of funneled ends of a pair of barb connectors with an O-ring disposed therebetween. The locking ends of the sanitary clamp includes a ratchet portion on one member and a housing member configured to lockingly receive the ratchet portion on the other member.

18 Claims, 4 Drawing Sheets

U.S. PATENT DOCUMENTS

| | | | |
|---|---|---|---|
| 5,305,978 A * | 4/1994 | Current | 248/230.4 |
| 5,318,546 A | 6/1994 | Bierman | |
| 5,590,859 A | 1/1997 | Lord | |
| 5,653,481 A * | 8/1997 | Alderman | 285/363 |
| 5,676,676 A | 10/1997 | Porter | |
| 5,697,942 A | 12/1997 | Palti | |
| 5,713,912 A | 2/1998 | Porter | |
| 5,729,872 A | 3/1998 | Ginocchio | |
| 6,101,684 A | 8/2000 | Ginocchio | |
| 6,113,062 A | 9/2000 | Schnell et al. | |
| 6,173,926 B1 | 1/2001 | Elvegaard | |
| 6,234,448 B1 | 5/2001 | Porat | |
| 6,261,254 B1 | 7/2001 | Baron et al. | |
| 6,390,721 B1 | 5/2002 | Wilson, II et al. | |
| 6,422,529 B1 | 7/2002 | Adelberg | |
| 6,523,866 B2 * | 2/2003 | Lin | 285/410 |
| 6,644,618 B1 | 11/2003 | Balbo | |
| 6,676,091 B2 | 1/2004 | Hauer | |
| 6,708,377 B2 * | 3/2004 | Maunder | 24/279 |
| 6,755,445 B2 * | 6/2004 | Balamuta et al. | 285/357 |
| 6,796,586 B2 | 9/2004 | Werth | |
| 7,284,731 B1 * | 10/2007 | Johnson et al. | 248/74.4 |
| 7,650,767 B2 * | 1/2010 | Robinson | 70/34 |
| 7,677,612 B2 * | 3/2010 | Maunder | 285/411 |
| 7,740,211 B2 * | 6/2010 | Dukes | 248/74.4 |
| 7,744,624 B2 | 6/2010 | Bettuchi | |
| 2003/0188401 A1 | 10/2003 | Huang | |
| 2004/0045447 A1 | 3/2004 | Navarro | |
| 2006/0131465 A1 | 6/2006 | Lynch, Jr. et al. | |
| 2006/0272369 A1 * | 12/2006 | Stachowiak, Jr. | 70/164 |
| 2008/0125811 A1 | 5/2008 | Bettuchi | |

OTHER PUBLICATIONS

Written Opinion of the International Searching Authority and International Search Report dated Sep. 3, 2009 from the corresponding International Application No. PCT/US2009/032230 filed Jan. 28, 2009.

* cited by examiner

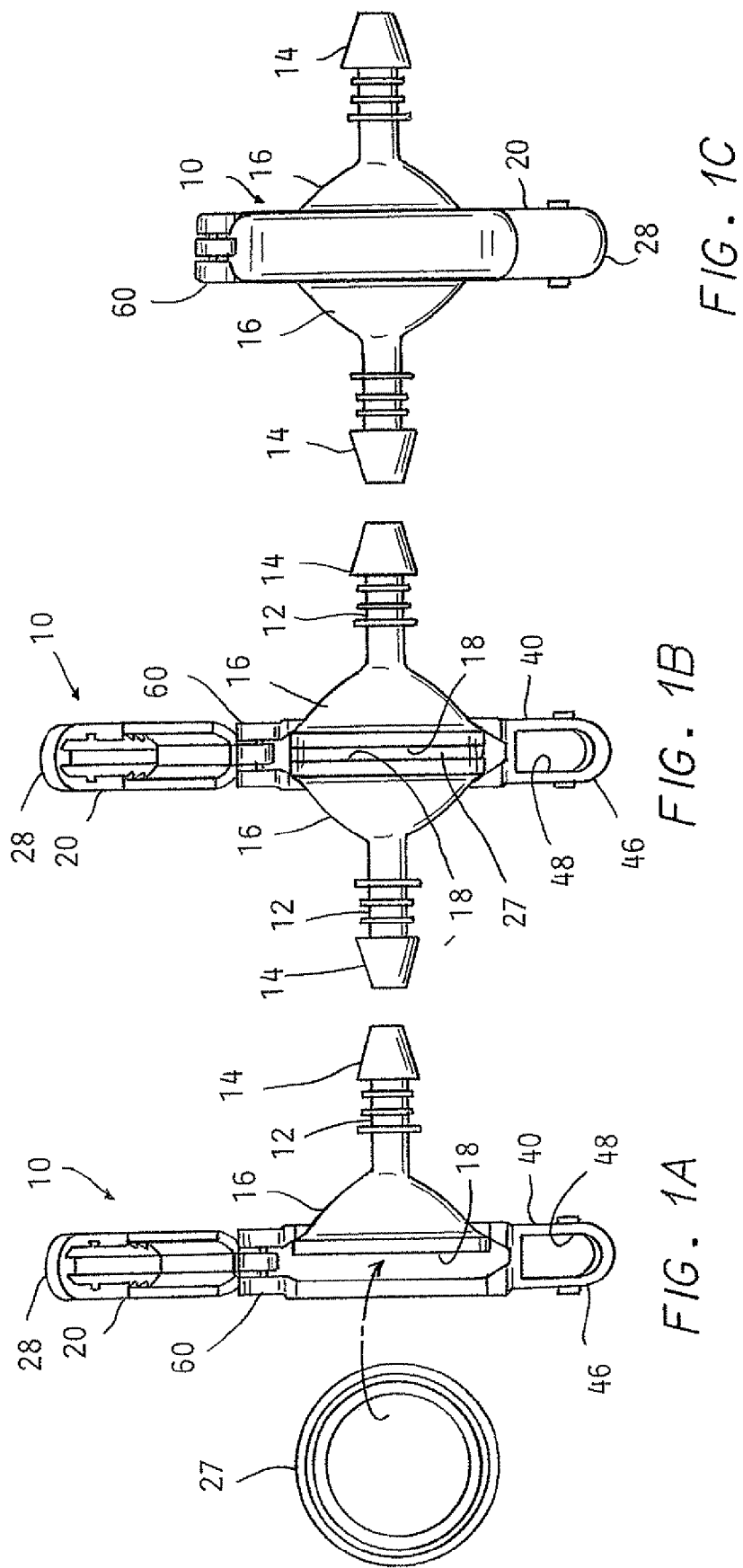

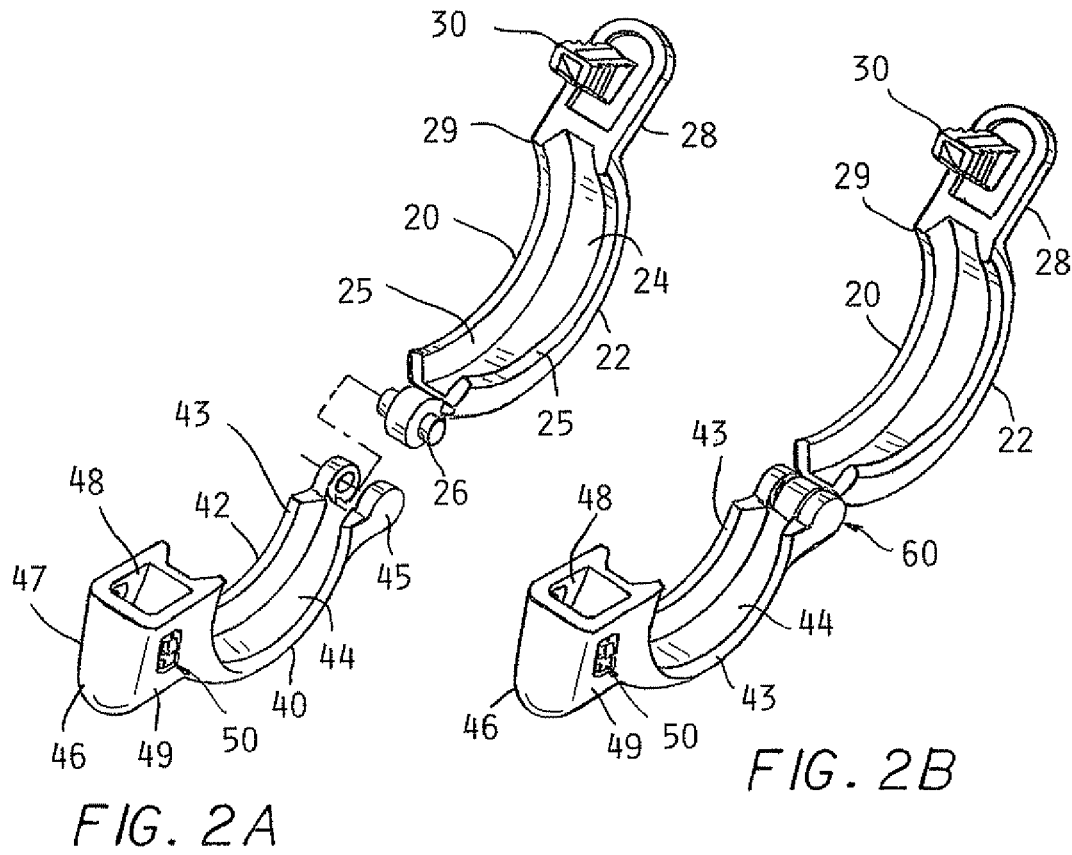
FIG. 2A
FIG. 2B
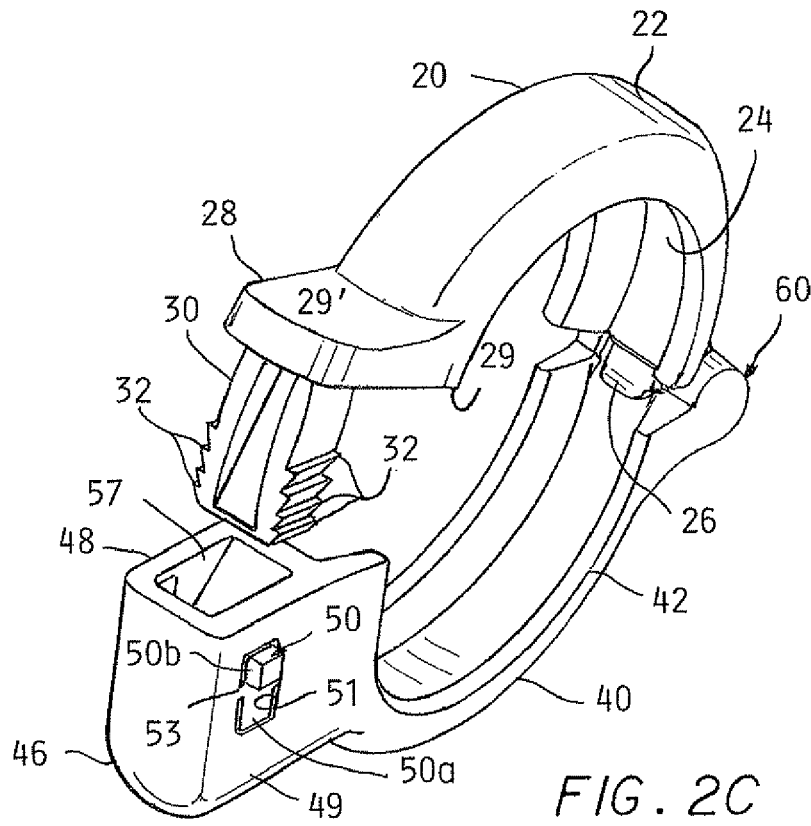
FIG. 2C

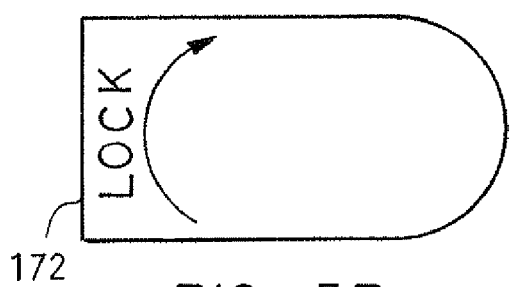
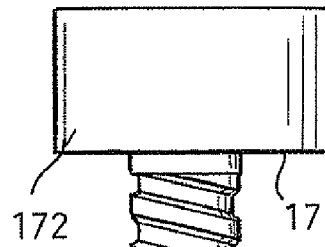
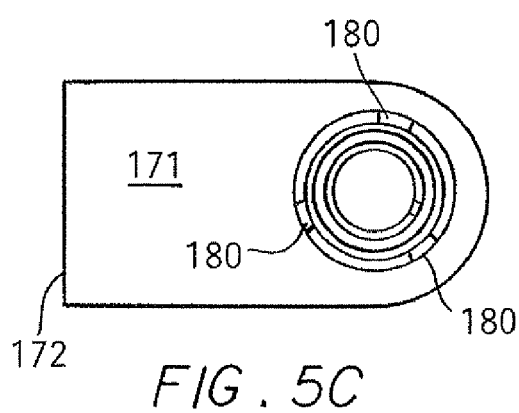
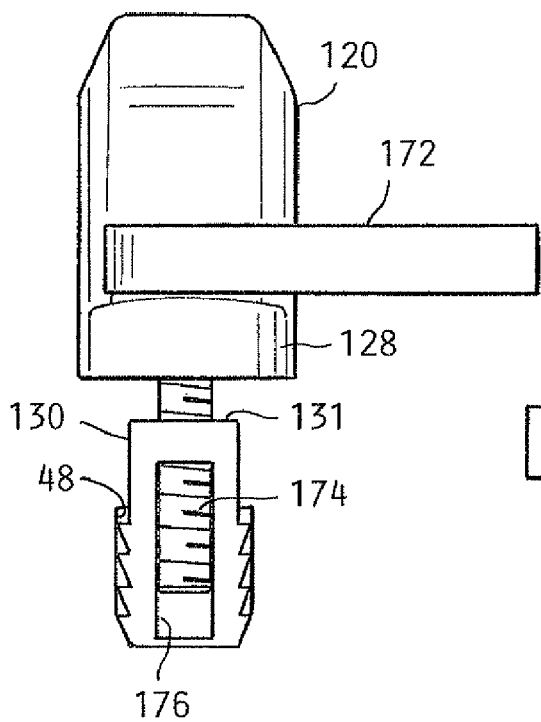
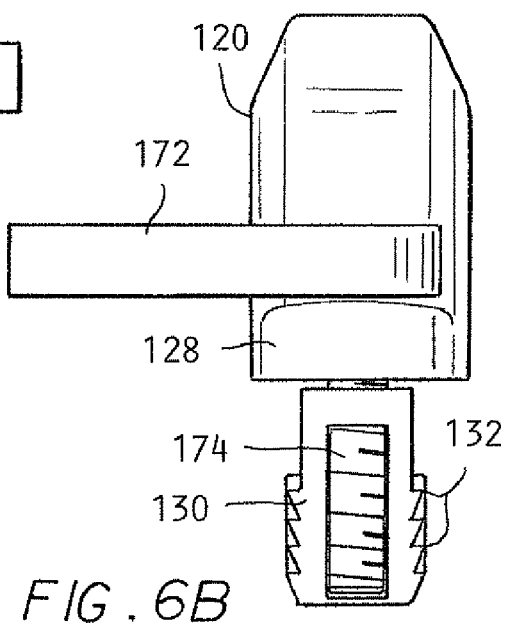

SANITARY CLAMP

This application claims priority of U.S. Provisional Patent Application Ser. No. 60/950,968 filed on Jul. 20, 2007 incorporated herein in its entirety by reference.

FIELD OF THE INVENTION

The invention relates to a disposable sanitary clamp for holding a pair of sanitary connections together.

BACKGROUND OF THE INVENTION

Flexible tubing made of plastic or rubber is widely used in the medical, pharmaceutical, biopharmaceutical, food and beverage and other laboratory environments. For certain assemblies involving connections from a medical instrument to a patient, stainless steel connectors or clamps have been used to connect ends of the flexible tubing together. Stainless steel connectors or clamps have the advantage of being capable of sterilization and therefore being reusable. However, stainless steel connectors are expensive to manufacture and do not completely protect against cross contamination.

It would be advantageous to provide a connector or clamp which is manufactured of a material that is resistant to solvents, acids, bases and heat and which is capable of use in applications requiring purity of the material. It would be advantageous to provide a clamp that a single use and disposable to eliminate potential cross contamination while providing superior sealing and/or connection for the flexible tubing.

SUMMARY OF THE INVENTION

The present invention addresses the aforementioned concerns as related to a clamp for connecting flexible tubing with funnel shaped barb connectors at one end. A sanitary clamp is provided for connection to a pair of barb connectors each having an end terminating at a funnel shaped portion. The sanitary clamp is made of a high molecular thermoplastic polymer to provide a cost efficient disposable clamp.

The sanitary clamp includes first and second semi-circular members in which when connected and locked together form a circular aperture for receiving the funnel shaped ends of the pair of connectors. Each of the first and second members also have second ends providing a locking device for selectively locking the first and second members together after the pair of barb connectors are disposed therein.

The locking device includes a ratchet with external teeth. The ratchet is connected to the first member. The locking device also includes a housing extending from the second end of the second member. The housing is configured to receive the ratchet. The housing has side walls with a rocker lock formed therein for defining a path of movement for locking and unlocking the teeth of the ratchet within the housing.

BRIEF DESCRIPTION OF THE DRAWINGS

The description herein makes reference to the accompanying drawings wherein like reference numerals refer to like parts throughout the several views, and wherein:

FIG. 1A is an elevational view of a sanitary assembly with one funnel shaped end of a barb connector disposed in and implementing a sanitary clamp according to the present invention, the sanitary clamp having a first and second member;

FIG. 1B is an elevational view of the sanitary assembly with an O-ring and pair of funnel shaped ends of barb connectors disposed in and implementing the sanitary clamp of FIG. 1A;

FIG. 1C is an elevational view of the sanitary assembly of FIG. 1B locked in the sanitary clamp;

FIG. 2A an exploded view of the sanitary clamp according to one embodiment of the invention;

FIG. 2B are perspective views of the sanitary clamp of FIG. 2A connected at a hinge;

FIG. 2C is front perspective view of the sanitary clamp in a partially closed position;

FIG. 5A is an elevational view of a locking knob of the sanitary clamp according to a second embodiment, the locking knob having a handle and acme thread;

FIG. 5B is a top view of the locking knob showing a top surface of the handle;

FIG. 5C is a bottom view of the locking knob;

FIG. 6A is a partial sectional view of the locking knob installed in a ratchet and the first member of the sanitary clamp in an unlocked position; and FIG. 6B is a partial sectional view of the locking knob in a locked position.

DETAILED DESCRIPTION OF THE PREFERRED EMBODIMENT

Figure 3A:
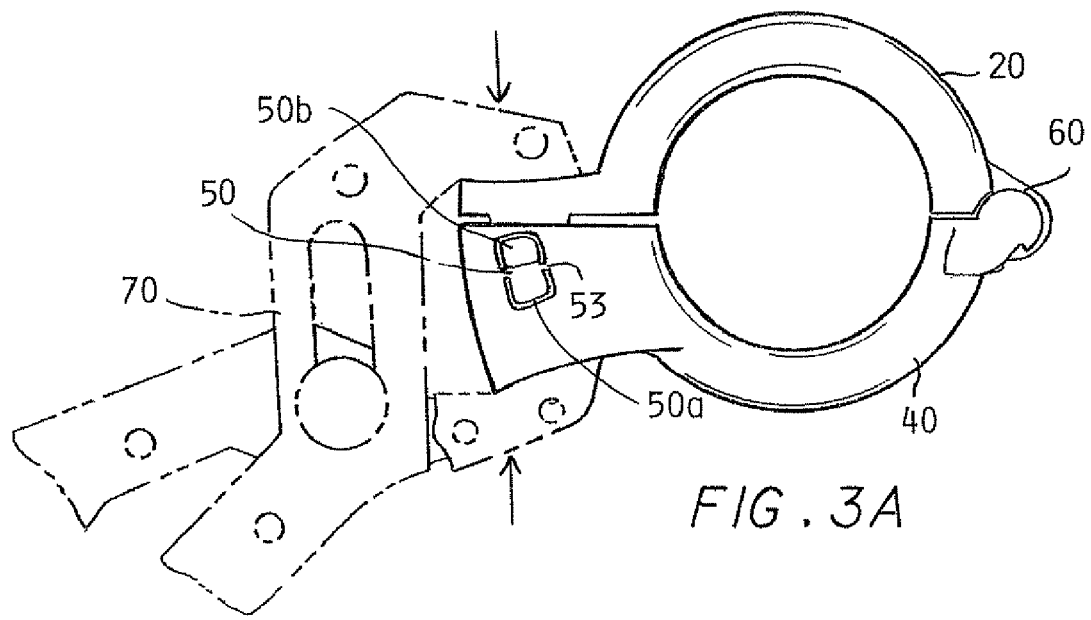
FIG. 3A is a side elevational view of a locking device of the sanitary clamp placed in the locked position by parallel closing pliers.

Referring to the Figures, the sanitary clamp 10 of the present invention is configured for connecting two sanitary connectors 12 having funnel shaped ends. A conventional sanitary connection includes a tubular member 12 having a barb connection 14 at one end for connection to a tube (not shown). The sanitary connection has an opposing end with a funnel formation 16 including an expanded circular opening at the terminating end 18.

The sanitary clamp 10, which fluidly and sealingly connects a pair of sanitary connections 12 together, is made of a high molecular weight thermoplastic polymer such as sold under the name of Kynar®, a registered trademark of Elf Atochem North America, Inc., a polyvinylidene difluoride, (PVDF) which is used generally in applications requiring the highest purity, strength, and resistance of solvents, acids, bases and heat. As an alternative, a polysulfone (PSU) is another preferred material.

The sanitary clamp is formed by a pair of semi-circular members 20, 40 connected together at a hinge 60. The first member 20 has a semi-circular portion 22 with an interior groove 24 formed between a pair of parallel side walls 25 on an interior surface and configured for receiving the funnel shaped ends 18 of a pair of sanitary connectors 12 with an O-ring seal 27 therebetween. At one end of the first member 20 adjacent to the arcuate portion 22 is an extending tab 26 forming a male portion of the hinge 60. On an opposing end of the first member 20 and attached to the arcuate, semi-circular 22 portion is an extending ledge 28 which extends essentially perpendicular from the end 29 of the semi-circular portion 22. The inner surface of the ledge 28 carries a ratchet 30 with external teeth 32 along opposing side edges of the ratchet.

The disposable sanitary clamp 10 further includes a second member 40 having a center semi-circular portion 42 forming an inner groove 44 on an internal surface between a pair of parallel side walls 43 and configured for receiving the O-ring seal 27 disposed between the pair of ends 18 of the sanitary connectors 12. The second member 40 has one bifurcated end 45 forming the female portion of the hinge 60. The first and second members 20 and 40 are connected together at the one end to form the hinge 60. The hinge 60 is conventionally formed for connection of end 26 of the first member to end 45 of the second member 40 to allow the clamp to rotate in place similar to a conventional metal clamp. The hinge 60 is configured to be positioned on the outside surfaces of the first and second members 20, 40 so as not to interfere with the disposition of the sanitary connectors 12 within the clamp 10.

The second member 40 has a housing 46 extending from the opposing end 47 spaced from the hinge portion 60. The housing 46 forms a well 48 therein for receiving the ratchet 30 of the first member 20. The housing 46 of the second member 40 has opposing sidewalls 49. The sidewalls 49 are mirror images of each other and therefore only one sidewall 49 will be discussed. In a center portion of the sidewall 49, a rocker lock 50 is formed therein. The rocker lock 50 is cut directly into each sidewall 49 leaving a gap/opening 51 around the rocker lock 50 except for connecting flanges 53 which connect a mid-section of the rocker lock 50 to the material of the sidewalls 49. The rocker lock 50 pivots about the connecting flanges 53. Manual pressure on either end of the rocker lock 50 will cause the opposite end of the rocker lock 50 to flex outward relative to the sidewalls 49. The gap/opening 51 is sized at the upper end 50b and lower end 50a to accommodate the teeth 32 on the ratchet 30 of the first member 20. The upper end of the rocker lock 50 forms an outwardly extending button 50b to facilitate the manual depression of the upper portion of the rocker lock 50 to release the ratchet 30 from the housing 46.

Figure 3B:
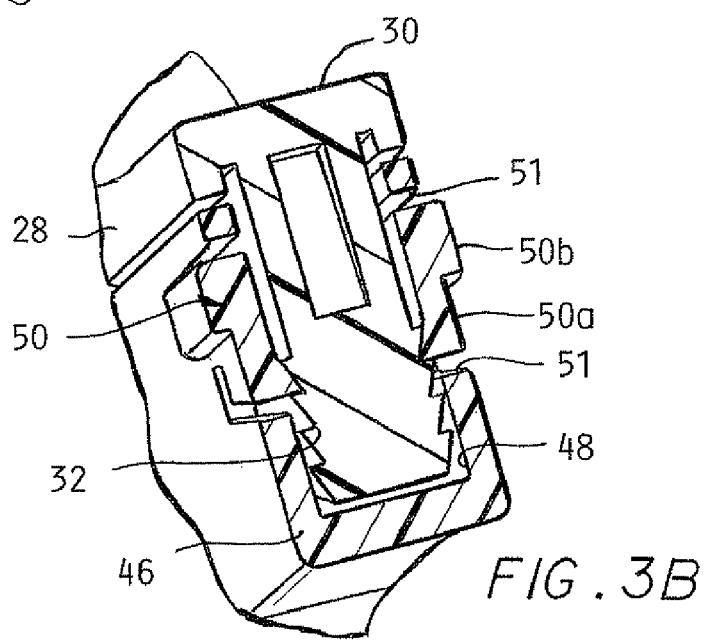
FIG. 3B is a sectional view of the locking device in a locked position.
Figure 4:
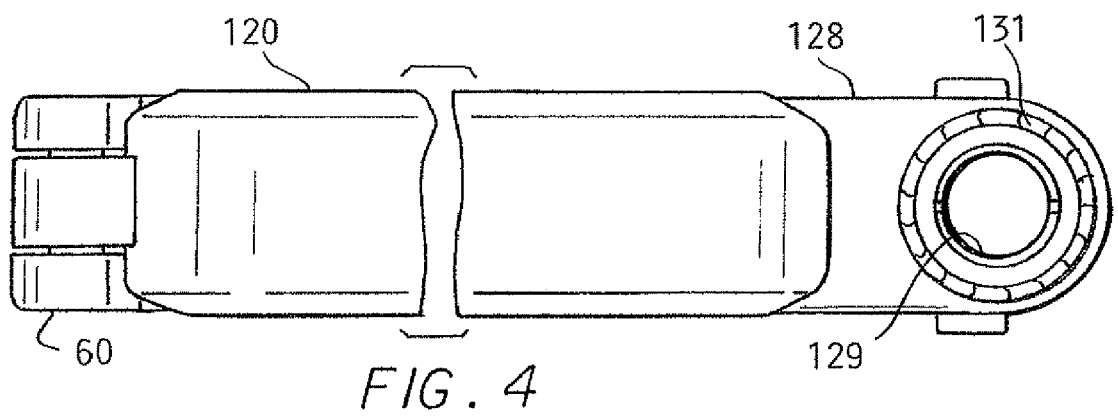
FIG. 4 is a top elevational view of a second embodiment of the first member of the sanitary clamp.

As manual downward pressure is applied to the first member 20, the teeth 32 on the ratchet 30 slide along the inner surface 57 of the rocker lock 50 (FIG. 2C). A pair of parallel closing pliers 70 as shown in FIG. 3A is used to complete the closure by depressing on the upper surface 29' ledge 28 and housing 46 of the first and second members 20, 40, respectively as illustrated by the arrows in FIG. 3, Once the teeth 32 are latched into the gaps 51 of the rocker locks 50, the teeth 32 cannot be released without depressing the top button portion 50b of the locks 50. To insure a secure lock of the teeth within the gaps 51, the teeth 32 are angled upward toward the ledge 28 of the first member 20 (FIG. 2C) to prevent easy pull out of the ratchet 30 from the housing 46.

An optional closure and locking mechanism are provided for the disposable sanitary clamp as shown in FIGS. 4-6C. In this next embodiment, the first member 120 is revised to include a through aperture 129 through the ledge 128. The aperture 129 is surrounded by a ribbed upper edge 131. The ribs on the upper edge 131 are spaced at 10° intervals. The second member 40 is unchanged.

The through aperture 129 is configured for receiving a locking knob 170 having a handle portion 172 integrally connected to an acme thread 174 extending from a bottom surface 171 of the handles 122. The ratchet 130 of the second embodiment has a center cavity 176 for receiving the acme thread 174. The acme thread 174 is configured to be inserted within the central cavity 176 of the ratchet member 130. The ratchet member 130 may be connected along its upper peripheral edge 131 to the bottom surface of the ledge 128. Alternatively, the ratchet member 130 can be a separate member initially separate from the ledge 128 and first member 120. In the alternative, the ratchet 130 is inserted into the well 48 of the housing 46 and then secured in place with the locking knob 170. The locking knob 170 functions to fully tighten the assembly beyond finger tight as would be done in the first embodiment by the pliers 70.

When the ratchet 130 having the acme thread 174 installed therein is positioned and manually pressured into connection with the well 48 of the second member 40, the handle 172 can then be moved clockwise so that the acme thread 174 pulls the ratchet 130 and the associated teeth 132 toward the rocker locks 50 for locking the teeth into the gaps 51 and thereby tightening the assembly beyond finger tight. FIG. 6A shows the closure in a full open position. FIG. 6B shows the closure in a locked position. When the closure is in a locked position, the housing 46 of the second member 40 is drawn up to the ledge 28 of the first member 120. The locked position of the handle 172 can be any point between 0 and 180 degrees in increments of 10 degrees from the open position via the ribbed upper edge 131 of the aperture 129 of the upper member 120. Integrally formed ratchet teeth 180 (FIG. 5B) on the bottom surface of the handle 172 of the locking knob 170 cooperating with the ribbed upper edge 131 of the first member 120 will prevent the handle 172 to unlock on its own.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed:

1. A sanitary clamp for connection to a pair of barb connectors each having one end terminating at a funnel shaped portion, the sanitary clamp comprising:
   a first member having a first semi-circular center portion disposed between a first end and a second end;
   a second member having a second semi-circular center portion disposed between a first end and a second end, said first ends of the first and second members configured to pivotally connect to each other such that said first and second members are pivotable to form a circular aperture configured to receive the funnel shaped portions of the pair of connectors and maintain the funnel shaped portions in a fluid tight relationship, said second end of the first member having a ledge orthogonally extending from the first semi-circular portion, said ledge coupled to a projection with a plurality of external ratchet teeth, said second end of the second member having a housing extending from the second semi-circular center portion and including a plurality of side walls defining a well positioned for orientation toward the ledge and configured for receiving the projection therein, at least two of the plurality of side walls each having a rocker lock formed therein, each rocker lock having a first portion, an opposed second portion including an engaging member and a flange therebetween pivotally connecting the rocker lock to its respective wall such that the second portion travels outwardly when the first portion is inwardly depressed, and wherein the rocker lock is configured to:
   resiliently position the engaging member in the well to releasably lock the projection when received in the well by engaging the engaging member with at least one of the plurality of external ratchet teeth; and permit retraction of the en a in member from the well when the first ortion is depressed to unlock the projection by releasing the engaging member from engagement with the at least one of the plurality of external ratchet teeth.

2. The sanitary clamp of claim 1 wherein the first and second semi-circular center portions each have a groove formed therein between a pair of walls, the groove configured to receive the funnel shaped portions of the pair of connectors and an O-ring disposed between the pair of funnel shaped portions.

3. The sanitary clamp of claim 2, wherein the projection has side walls extending orthogonally from the bottom surface of the ledge, said external ratchet teeth disposed on the side walls of the projection.

4. The sanitary clamp of claim 3, wherein the external ratchet teeth are angled upward toward the bottom surface of the ledge.

5. The sanitary clamp of claim 1, further comprising: a locking knob configured to couple the projection to the first member; wherein:
the locking knob extends through an aperture located in the ledge extending from the first member and includes a handle portion and a threaded portion disposed on opposing sides of the ledge.

6. The sanitary clamp of claim 5, wherein the threaded portion is configured for threaded engagement with a cavity defined by the projection in response to rotation of the handle portion of the handle.

7. The sanitary clamp of claim 6, wherein the handle portion is configured to engage the ledge while rotating such that the handle portion urges the ledge towards the housing as the threaded portion is threaded into the cavity when the projection is latched within the housing.

8. The sanitary clamp of claim 7, further comprising ratchet teeth formed on a bottom surface of the handle.

9. The sanitary clamp of claim 8, wherein the ratchet teeth on the bottom surface of the handle cooperate with a ribbed upper edge surrounding the through aperture of the first member to maintain the handle in a locked position.

10. The sanitary clamp of claim 1, wherein first portion includes a button portion extending outwardly with respect to the side wall, the button portion configured to facilitate depression of the first portion to release the engaging member from engagement with the engaged at least one of the plurality of external ratchet teeth when pressed.

11. A polymeric clamp for releasably connecting oppositely positioned terminating ends of a pair of sanitary connectors, comprising:
a first member connected to a second member by a pivot connection at a first end of each of the first and second members allowing for pivoting of the first member relative to the second member between an open position and a closed position, the first and second members spaced apart to receive the terminating ends in the open position and configured to retain the terminating ends in a fluid tight relationship in the closed position; and
a locking device for releasably locking second ends of the first and second members in the closed position, the locking device including a projection having a plurality of external ratchet teeth coupled to the second end of the first member and a housing defining a well on the second end of the second member configured for receiving the projection, wherein the second member includes a rocker lock having first portion, an opposed second portion including an engaging member and a flange therebetween pivotally connecting the rocker lock to a wall defining the well such that the second portion travels outwardly when the first portion is inwardly depressed, and wherein the rocker lock is configured to resiliently position the engaging member in the well to engage the at least one external ratchet tooth to latch the projection within the well and is configured to permit retraction of the engaging member with respect to the well to release the engaging member out of engagement with the at least one external ratchet tooth in response to depression of the first portion to unlatch the projection from the well.

12. The clamp of claim 11, wherein the projection is fixed to a ledge extending from the first member.

13. The clamp of claim 11, further comprising:
a locking knob configured to couple the projection to the first member; wherein:
the locking knob extends through an aperture defined by a ledge extending from the first member and includes a handle portion and a threaded portion disposed on opposing sides of the ledge,
the threaded portion is configured for threaded engagement with a cavity defined by the projection in response to rotation of the handle portion, and
the handle portion is configured to engage the ledge while rotating such that the handle portion urges the ledge towards the housing as the threaded portion is threaded into the cavity when the projection is latched within the housing.

14. The clamp of claim 11, wherein the first and second members define a continuous annular groove in the closed position for retaining the terminating ends in a fluid tight relationship.

15. The clamp of claim 14, wherein the annular groove is at least partially defined by a pair of opposing side walls configured to retain the terminating ends in a fluid tight relationship by engaging respective flanges included in the terminating ends.

16. The clamp of claim 14, wherein the annular groove is configured to receive an O-ring disposed between the terminating ends.

17. A sanitary assembly, comprising:
a pair of tubular barb connectors each having an open funnel shaped terminating end, wherein the terminating ends are oppositely positionable to define a continuous passage through the connectors;
a clamp composed of a thermoplastic polymer and configured to sealingly connect the terminating ends of the connectors such that the passage is fluid tight;
the clamp having a first member, a second member pivotally connected at a first end of each of the first and second members, and a locking device located at second ends of each of the first and second members; wherein:
the first and second members are pivotable relative to one other between an open position and a closed position, the first and second members configured to sealingly connect the terminating ends in the closed position, and
the locking device is configured for locking the first and second members in the closed position, the locking device including a projection having a plurality of external ratchet teeth coupled to the second end of the first member and a housing defining a well on the second end of the second member configured for receiving the projection, wherein the second member includes a rocker lock having a first portion, an opposed second portion including an engaging member and a flange therebetween pivotally connecting the rocker lock to a wall defining the well such that the second portion travels outwardly when the first portion is inwardly depressed, and wherein the rocker lock is configured to resiliently position the engaging member in the well to engage the at least one external ratchet tooth to latch the projection within the well and is configured to permit retraction of the engaging member with respect to the well to release the engaging member out of engagement with the at least one external ratchet tooth in response to depression of the first portion to unlatch the projection from the well.

18. The clamp of claim 17, further comprising:

a locking knob configured to couple the projection to the first member; wherein:

the locking knob extends through an aperture defined by a ledge extending from the first member and includes a handle portion and a threaded portion disposed on opposing sides of the ledge, the threaded portion is configured for threaded engagement with a cavity defined by the projection in response to rotation of the handle portion, and the handle portion is configured to engage the ledge while rotating such that the handle portion urges the ledge towards the housing as the threaded portion is threaded into the cavity when the projection is latched within the housing.

* * * * *

UNITED STATES PATENT AND TRADEMARK OFFICE
CERTIFICATE OF CORRECTION

PATENT NO. : 8,328,457 B2
APPLICATION NO. : 12/175712
DATED : December 11, 2012
INVENTOR(S) : Albert A. Werth Page 1 of 1

It is certified that error appears in the above-identified patent and that said Letters Patent is hereby corrected as shown below:

Column 5, Line 1, Claim 1, please delete "en a in" and insert therefor --engaging--

Signed and Sealed this
Fifth Day of March, 2013

Teresa Stanek Rea
*Acting Director of the United States Patent and Trademark Office*